(12) United States Patent
Yachia et al.

(10) Patent No.: US 10,631,966 B2
(45) Date of Patent: Apr. 28, 2020

(54) SYSTEM FOR SPHINCTERIC AND OTHER TISSUE REGENERATION

(71) Applicant: INNOVENTIONS LTD, Ohr Akiva (IL)

(72) Inventors: Daniel Yachia, Herzliya (IL); Yaara Arbel, Kibutz Beit Rimon (IL)

(73) Assignee: INNOVENTIONS LTD, Ohr Akiva (IL)

( * ) Notice: Subject to any disclaimer, the term of this patent is extended or adjusted under 35 U.S.C. 154(b) by 144 days.

(21) Appl. No.: 15/752,046

(22) PCT Filed: Aug. 9, 2016

(86) PCT No.: PCT/IL2016/050868
§ 371 (c)(1),
(2) Date: Feb. 12, 2018

(87) PCT Pub. No.: WO2017/025959
PCT Pub. Date: Feb. 16, 2017

(65) Prior Publication Data
US 2018/0228588 A1     Aug. 16, 2018

(30) Foreign Application Priority Data
Aug. 12, 2015   (IL) .......................................... 240541

(51) Int. Cl.
*A61F 2/04* (2013.01)
*A61F 2/06* (2013.01)
(Continued)

(52) U.S. Cl.
CPC ........ *A61F 2/0018* (2013.01); *A61B 17/0057* (2013.01); *A61B 17/42* (2013.01);
(Continued)

(58) Field of Classification Search
CPC ......... A61F 2/0018; A61N 1/00; A61M 37/00
(Continued)

(56) References Cited

U.S. PATENT DOCUMENTS

| 5,103,835 A | 4/1992 | Yamada |
| 6,238,335 B1 | 5/2001 | Silverman |

(Continued)

FOREIGN PATENT DOCUMENTS

| AU | 753618 B2 | 9/1999 |
| DE | 69726877 T2 | 10/2004 |

(Continued)

OTHER PUBLICATIONS

Luis Gustavo Morato de Toleo et al., "Continent vesicovaginal fistula", "einstein", Jan. 14, 2013, vol. 11(1), pp. 119-121, Link: https://www.ncbi.nlm.nih.gov/pmc/articles/PMC4872981/.

(Continued)

*Primary Examiner* — Suzettte J Gherbi
(74) *Attorney, Agent, or Firm* — Kaplan Breyer Schwarz, LLP

(57) ABSTRACT

The invention provides a system treating a weak or leaking urinary or other sphincter. The system includes two magnets and one or more devices to immobilize one of the magnets on a first side of the body organ to immobilize the other magnet on the second side of the body organ. The magnets may be positioned around the body organ with opposite poles facing each other. The invention may be used to induce the formation of muscle tissue of a sphincter such as a urethral sphincter or gastroesophageal sphincter, and also for mechanically occluding a leaking urethral or vesicovaginal fistula.

14 Claims, 7 Drawing Sheets

(51) Int. Cl.
  *A61F 2/00*  (2006.01)
  *A61N 2/06*  (2006.01)
  *A61N 2/00*  (2006.01)
  *A61B 17/00* (2006.01)
  *A61B 17/42* (2006.01)

(52) U.S. Cl.
  CPC .............. *A61F 2/04* (2013.01); *A61N 2/004* (2013.01); *A61N 2/06* (2013.01); *A61B 2017/00641* (2013.01); *A61B 2017/00876* (2013.01); *A61F 2002/044* (2013.01); *A61F 2210/009* (2013.01)

(58) Field of Classification Search
  USPC ........................................... 623/23.64–23.72
  See application file for complete search history.

(56) References Cited

U.S. PATENT DOCUMENTS

| | | | |
|---|---|---|---|
| 6,293,923 B1 | 9/2001 | Yachia et al. | |
| 6,455,568 B2 | 9/2002 | Jenkins | |
| 6,604,004 B1 | 8/2003 | zelickson | |
| 6,613,047 B2 | 9/2003 | Edwards | |
| 7,261,722 B2 | 8/2007 | McGuckin | |
| 7,328,070 B2 | 2/2008 | Gerber | |
| 7,368,279 B2 | 5/2008 | Bitar | |
| 8,068,910 B2 | 11/2011 | Gerber | |
| 8,478,411 B2 | 7/2013 | Gerber | |
| 8,538,534 B2 | 9/2013 | Soffer | |
| 9,387,338 B2* | 7/2016 | Burnett | A61N 1/0492 |
| 10,105,132 B2* | 10/2018 | Lamson | A61F 2/82 |
| 10,206,674 B2 | 2/2019 | Kawaura | |
| 2002/0111586 A1 | 8/2002 | Mosel | |
| 2005/0131442 A1 | 6/2005 | Yachia et al. | |
| 2007/0049879 A1 | 3/2007 | Gutierrez | |
| 2011/0160765 A1 | 6/2011 | Melmed | |
| 2012/0035410 A1 | 2/2012 | Borgos et al. | |
| 2013/0096645 A1 | 4/2013 | Shadduck | |
| 2013/0325143 A1* | 12/2013 | Lamson | A61F 2/82 623/23.66 |
| 2014/0107726 A1 | 4/2014 | Voznesensky et al. | |
| 2015/0165226 A1* | 6/2015 | Simon | A61N 1/40 600/13 |
| 2015/0313995 A1* | 11/2015 | Hung | A61M 37/0069 600/12 |
| 2017/0360594 A1 | 12/2017 | Park | |
| 2018/0036550 A1* | 2/2018 | Jin | A61N 1/326 |
| 2018/0265858 A1* | 9/2018 | Souza | B82Y 5/00 |
| 2019/0242881 A1* | 8/2019 | Souza | G01N 33/5082 |

FOREIGN PATENT DOCUMENTS

| | | | | |
|---|---|---|---|---|
| EP | 0701415 B1 | 3/1996 | | |
| EP | 0788813 A1 | 8/1997 | | |
| EP | 0923357 B1 | 6/1999 | | |
| JP | 4904156 B2 | 12/2006 | | |
| JP | 4884368 B2 | 10/2007 | | |
| WO | 2011053607 A1 | 5/2011 | | |
| WO | WO-2011053607 A1 * | 5/2011 | ........... A61N 1/0502 |
| WO | 2016185479 A1 | 11/2016 | | |

OTHER PUBLICATIONS

Anupender Singh Sidhu et al., "Neuro-regulation of lower esophageal sphincter function as treatment for gastroesophageal reflux disease", "World Journal of Gastroenterology", Feb. 21, 2008, vol. 14(7), pp. 985-990, ISSN 1007-9327, Link: https://www.ncbi.nlm.nih.gov/pmc/articles/PMC2689423/.

Glenn S. Gerber et al., "Female Urinary Tract Fistulas", "The Journal of Urology", Publisher: American Urological Association, Inc., vol. 149, pp. 229-236, dated Feb. 1993, Link: https://www.sciencedirect.com/sdfe/pdf/download/eid/1-s2.0-S0022534717360457/first-page-pdf.

Sandip P Vasavada, MD, "Vesicovaginal and Ureterovaginal Fistula", "Medscape", updated Dec. 18, 2018, Link: https://emedicine.medscape.com/article/452934-overview.

Officer Liya Orenshtein-Vilensky, "International Search Report and the Written Opinion", International Patent Application PCT/IL2016/050868, Date Complete Dec. 4, 2016, 12 pp.

Coletti et al., "Cytometry Part A, Static Magnetic Fields Enhance Skeletal Muscle Differentiation In Vitro by Improving Myoblast Alignment", 2007, pp. 846-856, ISAC.

Schafer et al., "Functional investigations on human mesenchymal stem cells exposed to magnetic fields and labeled with clinically approved iron nanoparticles", BMC Cell Biology, 2010, 17 pp.

United Nations General Assembly, "Supporting efforts to end Obstetric Fistula", Aug. 5, 2014, 19 pp., Sixty-ninth session, A/69/256.

\* cited by examiner

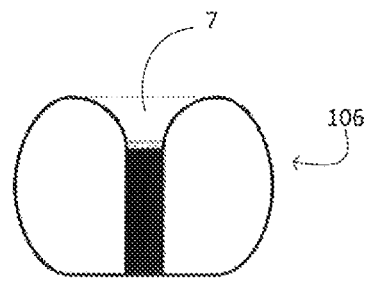
Fig. 3a
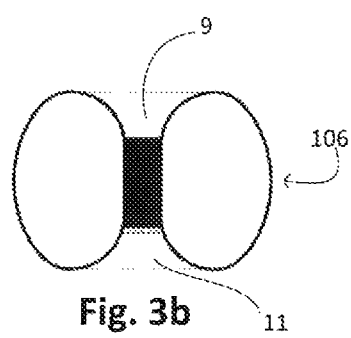
Fig. 3b
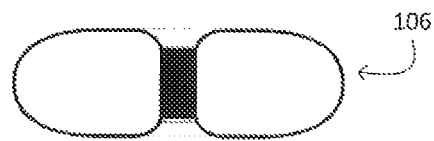
Fig. 3c
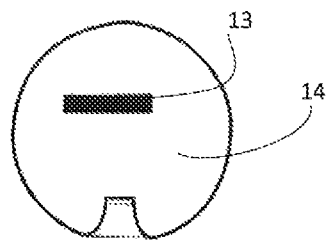
Fig. 3d
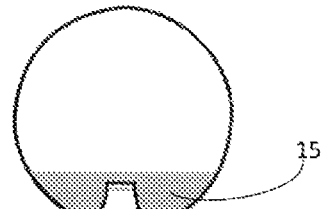
Fig. 3e
Fig. 3

Fig. 4a (Control)

Fig. 4b (One magnet)

Fig. 4c (Two magnets)

SYSTEM FOR SPHINCTERIC AND OTHER TISSUE REGENERATION

FIELD OF THE INVENTION

The present invention relates to medical devices.

BACKGROUND OF THE INVENTION

The following prior art publications are considered to be relevant for an understanding of the prior art:

U.S. Pat. No. 6,293,923.

Coletti et al Cytometry Part A, 71A:846-856, 2007.

Report of the UN Secretary-General. 69th Session of the General Assembly, Aug. 5, 2014—A/69/256: Supporting efforts to end obstetric fistula.

US Patent Application 2005/0131,442.

Involuntary urine leakage from the bladder can result from various causes which can be generally divided into two groups:

Anatomical causes such as destruction or under-functioning of the urethral sphincteric mechanism or development of a vesicovaginal, vesicouterinal or ureterovaginal fistula. Sensorial causes include reduction in the functional capacity of the bladder creating an uncontrollable urge to void that may induce uncontrollable urination.

Several surgical and non-surgical methods, such as urethral slings for preventing urethral descent in severe stress urinary incontinence (SUI) cases, and various vaginal pessaries for urethral compression for lighter cases, have been developed.

The gastroesophageal sphincter is a muscular entity sealing the esophagus from the stomach. Normally, the sphincter opens during swallowing, allowing food to enter into the stomach. The rest of the time, it closes tightly to prevent food and acid in the stomach from backing up into the esophagus.

Gastroesophageal reflux disease (GERD) is a digestive disorder in which the gastroesophageal sphincter does not seal tightly, and remains relaxed between swallows. This allows gastric contents, including acidic digestive juices, to enter the esophagus and irritate the esophagus. If GERD is not treated, it can permanently damage the esophagus or even lead to the development of a cancerous growth at the esophagus. Many things can weaken or loosen the lower esophageal sphincter including certain foods, smoking, alcohol, many medications, increased abdominal pressure due to of obesity or pregnancy, and a weakening of the diagraphragmatic muscle causing part of the stomach to bulge and protrude above the diaphragm (hiatal hernia) and disrupt the functioning of the sphincter.

The term "vesicovaginal fistula" refers to the presence of a fistula or passageway between the urinary bladder and the vagina and it is the most common urogenital fistula. This causes constant leakage of urine form the bladder into the vagina and out from the vagina and results in frequent vaginal and vulvar irritation and bladder infections. Vesicovaginal fistulae require surgical repair by experienced surgeons. In the developed world, such fistulas are uncommon and usually result from complications of gynecological surgery, pelvic abscess or pelvic irradiation. In poor developing countries however, these fistulas are more common and are related to obstructed labor due to unattended deliveries, small pelvic dimensions, malpresentation, poor uterine contractions and introital stenosis, especially in very young girls. In some parts of Africa, it is estimated that in as many as 3-4 per 1000 vaginal deliveries women develop these fistulas. A 2014 report of the United Nations Secretary-General states: "Obstetric fistula is a devastating childbirth injury that leaves women incontinent and often stigmatized and isolated from their families and communities." "The odour from constant leakage, combined with misperceptions about its cause, often results in stigma and ostracism. Many women with fistula are abandoned by their husbands and families. They may find it difficult to secure income or support, thereby deepening their poverty." (Report of the UN Secretary-General. 69th Session of the General Assembly. Aug. 5, 2014—A/69/256: Supporting efforts to end obstetrric fistula) Non-surgical therapy for vesicovaginal fistulas is rarely effective; and most vesicovaginal fistulas require surgery by experts to close the opening usually through the abdomen or vagina. In certain cases it can be treated with laparoscopic or robotic surgery.

Conservative treatments for mild SUI are based on pelvic floor musculature reinforcement either by electrical stimulation or by other physiotherapeutic means such as Kegel exercises, approaches that need close and active cooperation of the patients.

Although severe SUI and pelvic floor descensus cases can be successfully treated with surgery based on implantation of natural fascial slings or artificial mesh slings, in about 30-40% of SUI cases the incontinence recurs within 5-10 years mostly due to age-related hormonal deficiency causing weakening of the pelvic floor muscle.

Extracorporeal magnetic stimulation created by pulsating magnetic fields or a single magnetic field has been shown to induce muscle tissue formation in tissue cultures (Coletti et al. Cytometry Part A, 71A:846-856, 2007).

SUMMARY OF THE INVENTION

In one of its aspects, the present invention provides a system for the treatment of a weak or leaking urethral sphincter, for example, in cases of anatomical urinary incontinence in a male or female individual. An external element comprises a first magnet and is adapted for immobilization on the external body surface adjacent to the down-stream side of the urethra, below the sphincter, i.e. at the perineum in male patients and the vulva in female patients. A vesicular element comprises a second magnet and is configured to float in the urinary bladder above the bladder end of the urethral sphincter. In the case of advanced urinary incontinence, the strength of the magnets can be increased to pull the vesicular element toward the bladder outlet to immobilize it and create a mechanical occlusion of the urethra as described in U.S. Pat. No. 6,293,923.

The present invention is based on the novel finding that placing muscle tissue between two magnets can induce the formation and acceleration of proliferation of muscle tissue, when the magnets are oriented so that opposite poles of the two magnets are facing each other. With this orientation, the magnetic field lines pass through the tissue between them. The inventors have found that placing precursor muscle cells in a magnetic field generated by two, oppositely oriented NdFeB.45 magnets (5×20×50 mm), where the muscle cells are positioned between the two magnets, can induce the organization and proliferation of muscle tissue. The inventors have also observed induction of sphincteric muscle tissue strengthening in vivo upon exposure of the tissue to two magnetic fields.

In another of its aspects, the present invention provides a method and system for inducing the formation of muscle and other tissues in a body organ. The system of the invention comprises two or more magnets and a device for maintaining the magnets on opposite sides of the tissue to be treated. Preferably, the two magnets are maintained with opposite poles facing each other.

In one embodiment of the invention, the system of the invention is adapted for use in the treatment of a fresh vesicovaginal fistula in a female individual. In this embodiment, a vaginal element comprises a first magnet and is adapted to be retained in the vagina adjacent to the vaginal side of the fistula. A vesicular element comprises a second magnet and is configured to be inserted into the urinary bladder on the bladder side of the fistula to create an opposed magnetic field through the fistula and induce an acceleration in tissue regeneration that may close the fresh fistula tract without a surgical procedure. In the case of epithelialization of the fistula tract, before application of the opposed magnetic field, the mucosal cover of the fistula tract may be brushed out using a "fistula brush" to create raw tissues along the fistula tract. The strength of the magnets can be increased to pull the vesicular element toward the bladder opening of the fistula to immobilize it and create a mechanical occlusion of the fistula tract during the tissue regeneration period.

In yet another embodiment, the invention is adapted for the treatment of a weak gastroesophageal sphincter, for example, in cases of gastroesophageal reflux disease (GERD) in a male or female individual. In this embodiment, a ventral element comprises a first magnet that is adapted for positioning on the ventral surface of the individual over the gastroesophageal sphincter, and a dorsal element comprises a second magnet that is adapted for positioning on the back of the individual over the sphincter to create an opposed magnetic field through the gastroesophageal sphincter.

BRIEF DESCRIPTION OF THE DRAWINGS

In order to understand the invention and to see how it may be carried out in practice, a preferred embodiment will now be described, by way of non-limiting example only, with reference to the accompanying light micrographs and drawings, in which:

FIGS. 3a to 3e show, in cross section, five examples of possible shapes for the expanded vesicular element of the system of FIG. 2.: a spherical shape with a single dimple (FIG. 3a), a spherical shape with two dimples (FIG. 3b), a flattened disc (FIG. 3c), a spherical shape with a magnet inside the lumen of the vesicle element (FIG. 3d), and a spherical shape with a ferromagnet (FIG. 3e);

DESCRIPTION OF THE INVENTION

Figure 1:
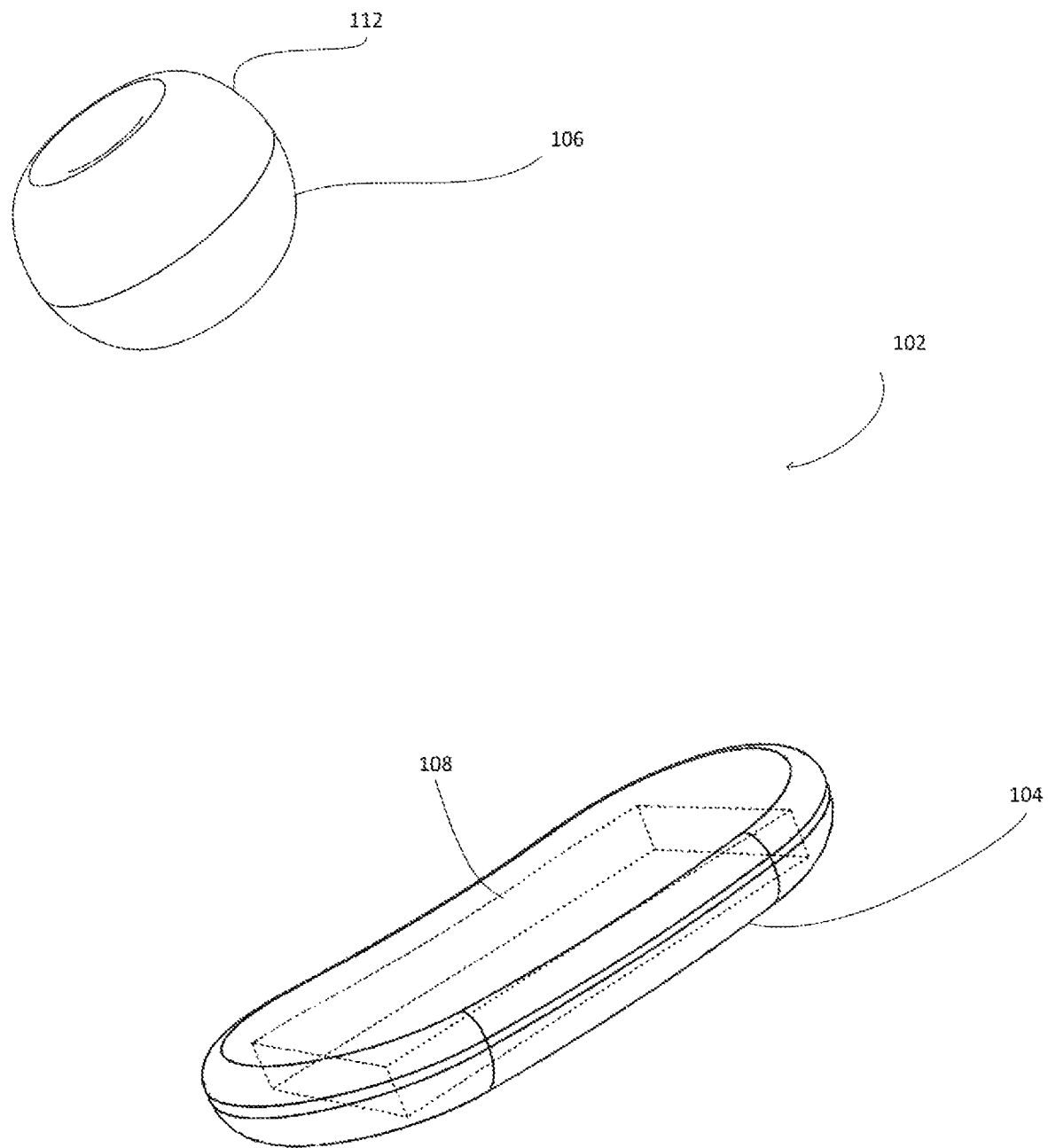
FIG. 1 shows a system for the treatment of a weak sphincter of a urinary bladder, in accordance with one embodiment of the invention.

FIG. 1 shows a system 102 for the treatment of a weak urethral sphincter, for example, in cases of urinary incontinence in a male or female individual, in accordance with one embodiment of the invention. In the case of a male individual, urinary incontinence may be the result of prostate surgery which can result in injury to the urethral sphincter. The system 102 comprises an external element 104 and a vesicular element 106. The external element is adapted for immobilization on an external body surface below the urinary bladder, for example, at the vulva in female patients and at the perineal area in male patients. The external element 104 may be incorporated into a garment, such as sling or underpants that is worn by the individual. The external element 104 comprises one or more magnets 108. The vesicular element 106 is a balloon configured to be filled in the urinary bladder, and examples of the vesicular element 106 are shown in cross-section in FIGS. 3a to 3e. The vesicular element 106 has a thin wall 112 surrounding a lumen. The wall 112 of the vesicular element 106 may be made from any flexible biocompatible material, such as a medical grade silicone or medical grade silicone containing small ferromagnetic particles. A self-sealing valve in the wall 112 allows the lumen to be filled with a gas or a fluid lighter than urine in order to bring the vesicular element to its expanded and floating configuration, as described below. When the lumen is empty, the vesicular element 106 can be collapsed for delivery into the urinary bladder through the urethra, and then filled with a fluid until the vesicular element 106 attains its expanded configuration inside the bladder. The vesicular element 106 has a vesicular magnet (not shown in FIG. 1) that may be, for example, embedded in the wall 112 or located in the lumen of the vesicular element 106. The magnet in the lumen can be a ferrofluid composed of small magnetic particles suspended in a carrier fluid such as mineral oil. Expandable balloons suitable for insertion and retention in a urinary bladder are described, for example, in U.S. Pat. No. 6,293,923.

The vesicular element 106 is inserted into the lumen of the urinary bladder in an empty and collapsed state and is filled inside the bladder by injection of an expansion fluid into the lumen of the vesicular device through the self-sealing valve. US Patent Publication 2010-0016834 discloses a delivery device that may be used for delivering the vesicular element 106 in its empty and collapsed state through the urethra into the urinary bladder and filling the vesicular element with the expansion fluid. For removal of the vesicular element from the bladder, the wall of the vesicular element may be pierced to evacuate the expansion fluid and allow the vesicular element to be collapsed for removal. US Patent Publication 2010-0016834 discloses a retrieval device that may be used for piercing the wall of the vesicular device to evacuate the expansion fluid and for removing the vesicular element from the bladder through the urethra.

Figure 2:
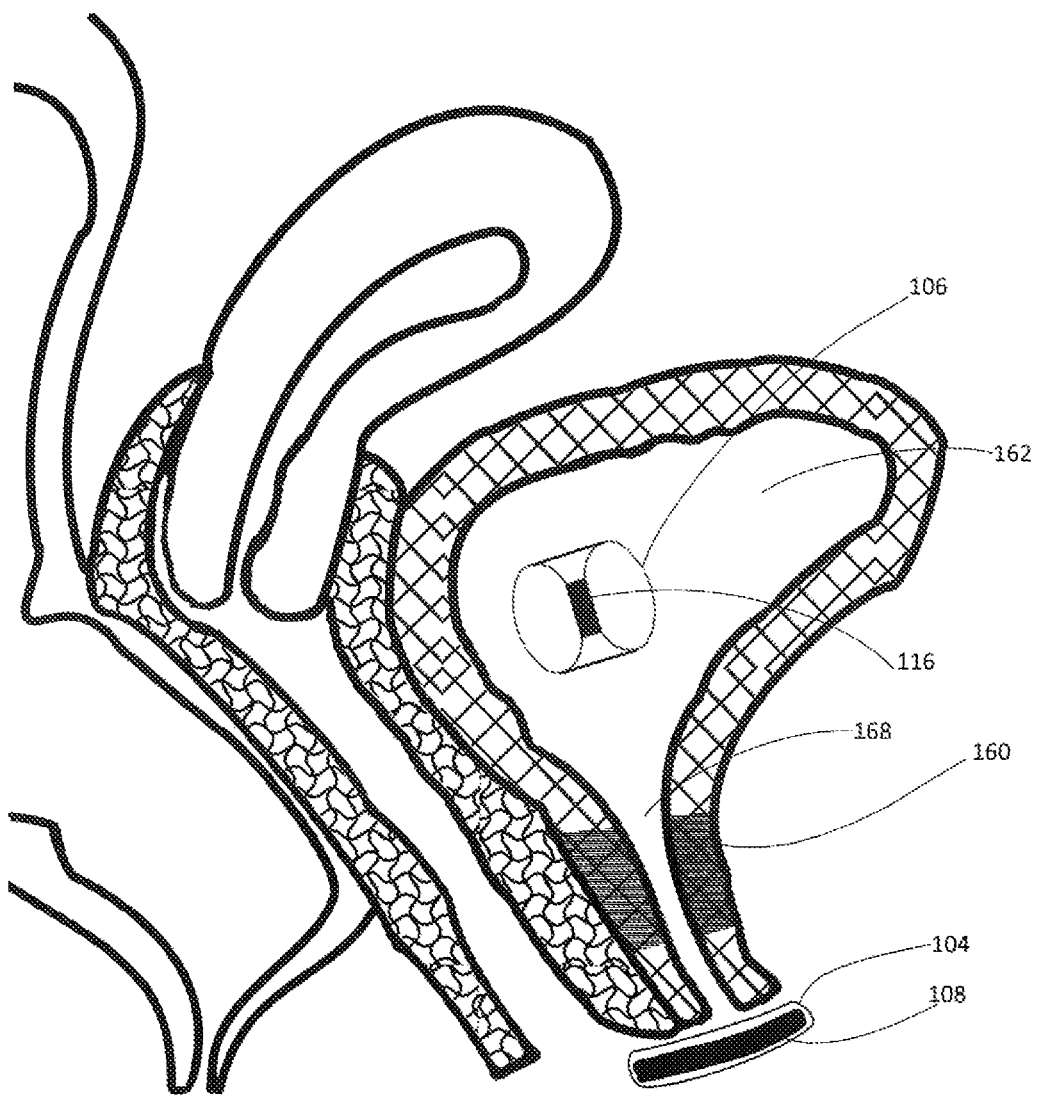
FIG. 2 shows use of the system of FIG. 1 in the treatment of a weak urethral sphincter of a urinary bladder of a female individual.

FIG. 2 shows use of the system 102 in the treatment of a weak urethral sphincter 160 of a urinary bladder 162 of a female individual. Use of the system 102 in the treatment of a weak urethral sphincter in a male individual is similar. The vesicular element 106 has been inserted into the urinary bladder 162 and filled inside the bladder to allow the vesicular element 106 to attain its expanded configuration and float in the urine, as explained above. The magnet 108 of the external element 104 has been immobilized on the body surface below the bladder 162 by means of a sling or garment (not shown in FIG. 2) worn by the individual.

The external magnet 108 and the vesicular magnet 116 are positioned with opposite poles facing each other. The magnet of the external element and the magnet of the vesicular element will typically be separated by about 4 to 6 cm in use (FIG. 2). In this case, the magnetic field between the magnet of the external element and the magnet of the vesicular element may have a strength, for example, of about 800 Gauss for anchoring the vesicular element in the vicinity of the bladder outlet. The opposed magnetic field created by the two magnets 108 and 116 above and below the sphincteric tissues may induce tissue regeneration of the sphincter, which may tend to strengthen the sphincter and reduce or eliminate urinary leakage. Additionally, if needed, by using stronger magnets, the vesicular element 106 can be drawn towards the bladder opening 168 so as to seal the bladder opening 168 and prevent urine leakage.

The shape of the vesicular element 106 when expanded is selected to fit the indication for which it is used, either to strengthen the sphincter, regenerate tissue or occlude a passage. The vesicular element 106 may have any shape when expanded. FIGS. 3a to 3e show, in cross section, five possible shapes for the expanded vesicular element. The expanded configuration of the vesicular element 106 may be, for example, a spherical shape with a single dimple 7 (FIG. 3a), a spherical shape with two dimples 9 and 11 (FIG. 3b), a flattened disc (FIG. 3c), a spherical shape with a magnet 13 inside the lumen 14 of the vesicle element (FIG. 3d), or a spherical shape with a ferromagnet 15 (FIG. 3e). The vesicular element 106 may also have a polyhedral shape (not shown).

Any biocompatible fluid may be used as a filling fluid to expand the vesicular element 106. Preferably, the filling fluid imparts to the expanded vesicular element 106 a specific gravity that is less than the specific gravity of urine, so that the expanded vesicular element 106 floats in urine. For example, the filling fluid may be sterilized air, or a biocompatible oil such as mineral oil/liquid paraffin, vegetable oil or other oily substances. In one presently preferred embodiment, the wall 112 of the vesicular element 106 is made from a medical grade silicone and the filling fluid is light mineral oil. The inventors have found that when the wall 112 of the vesicular element 106 is made from silicone, light mineral oil in the lumen of the vesicular element 106 can slowly seep through the wall 112 of the vesicular element 106 and form a thin and smooth coating with zero stress on the exterior surface of the vesicular element 106 that tends to reduce or prevent the formation of biofilm and crystal adhesion on the vesicular element 106 which can cause infections.

An experiment was conducted in order to investigate and determine the effect of an opposed magnetic field generated between two opposed magnets on a monolayer of muscle cell precursors. C2C12 cells were seeded at a density of 15,000 cell/cm2 and incubated for 4 days. One cell culture was placed above a static magnet. A second cell culture was placed between two opposed static magnets (north pole facing south pole). A third cell culture was a control culture not exposed to a magnetic field. The magnets used were rectangular NdFeB.45 magnets (5×20×50 mm). The magnetic field measured from a single magnet was 800 Gauss and the distance between the 2 magnets was 5 cm which is about the distance between the vulva and the lower part of the bladder. After 4 days of incubation, the cells were fixed with 4% PFA (paraformaldehyde) and stained with FITC-conjugated Phalloidin (for Actin fibers, which appear green in micrographs), DAPI (for cell nuclei, which appears blue in micrographs) and Desmin (for muscle, which appears red in micrographs). Images were taken with a fluorescent microscope at random fields of the samples at magnifications of 20×, 40× and 100×.

Figure 4:
FIG. 4a shows a microscopic image of a cell culture of C2C12 cells not exposed to a magnetic field.
FIG. 4b, shows a microscopic image of a cell culture of C2C12 cells exposed to a magnetic field of a single magnet.
FIG. 4c shows a microscopic image of a cell culture of C2C12 cells exposed to the magnetic field between two magnets with opposite poles facing each other.
Figure 4:
Figure 4:

FIG. 4 shows images of a cell culture of C2C12 cells not exposed to a magnetic field (FIG. 4a), exposed to a magnetic field of a single magnet (FIG. 4b), and exposed to the magnetic field between two magnets (FIG. 4c). Cells exposed to a magnetic field either above a single magnet (FIG. 4b), or between two magnets (FIG. 4c), showed enhanced maturation in comparison with cells not exposed to a magnetic field (FIG. 4a), which was expressed by the formation of multinucleated myotubes. In these cultures, the cells showed an aligned orientation. Formation of myotubes was greatest in the cultures placed between two magnets (FIG. 4c).

Figure 5A:
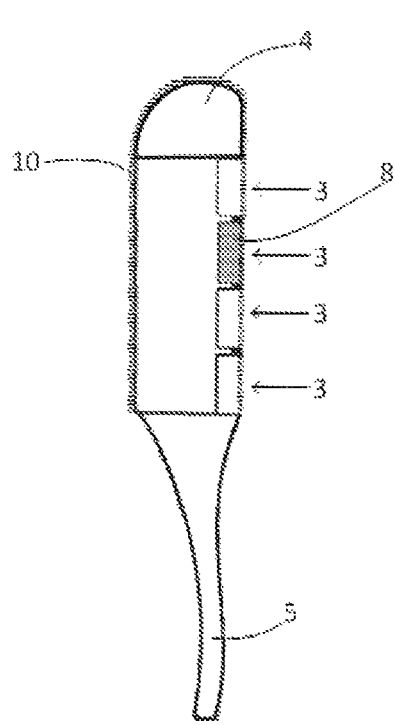
FIGS. 5a and 5b show a system for the treatment of a vesicovaginal fistula in a female individual, in accordance with one embodiment of this aspect of the invention.
Figure 5B:
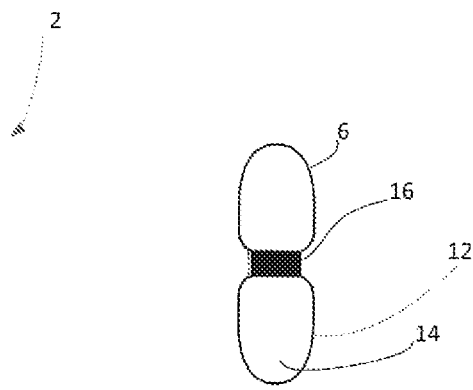
Figure 6:
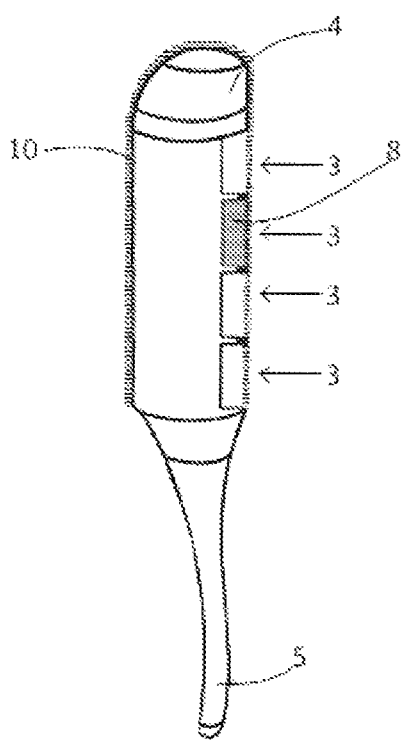
FIG. 6 shows a perspective view of the vaginal element of the system of FIG. 5.

FIGS. 5a and 5b show a system 2 for the treatment of a newly occurred fresh, or an old vesicovaginal fistula in which its mucosal cover has been removed using a fistula brush, in a female individual, in accordance with one embodiment of this aspect of the invention. The system 2 comprises a vaginal element 4 and a vesicular element 6 The vaginal element, shown in cross-sectional view in FIG. 5a and in perspective view in FIG. 6, is designed for insertion and retention in a vagina. Insertion and removal of the vaginal element is facilitated by a handle 5. The vaginal element comprises one or more magnet retention sites 3 on its surface where a vaginal magnet 8 may be inserted and retained. Four retention sites are shown in FIGS. 5a and 6. This is by way of example only, and the vaginal element may have any number of retention sites. The vaginal element including its magnetic element 8 is enclosed in a biocompatible coating 10. The coating 10 is selected to promote retention of the vaginal element in the vagina and to be easily cleanable and comfortable to the individual. The coating 10 can be made of a disposable material.

The vesicular element 6 is a balloon configured to be filled in the urinary bladder of the individual, and is shown in cross section in FIG. 5b. The vesicular element 6 has a thin wall 12 surrounding a lumen 14. The wall 12 of the vesicular element 6 may be made from any flexible biocompatible material, such as a medical grade silicone. A self-sealing valve in the wall 12 allows the lumen 14 to be filled with a fluid in order to bring the vesicular element to its expanded configuration, as described below. When the lumen 14 is empty, the vesicular element 6 can be collapsed for delivery into the urinary bladder through the urethra, and then filled with a fluid until the vesicular element 6 attains its expanded configuration inside the bladder. The vesicular element 6 has a vesicular magnet 16 that may be, for example, embedded in the wall 12 or located in the lumen 14 of the vesicular element 6. The magnet in the lumen can be a ferrofluid composed of small magnetic particles suspended in a carrier fluid such as mineral oil. Expandable balloons suitable for insertion and retention in a urinary bladder are described, for example, in U.S. Pat. No. 6,293,923.

Figure 7:
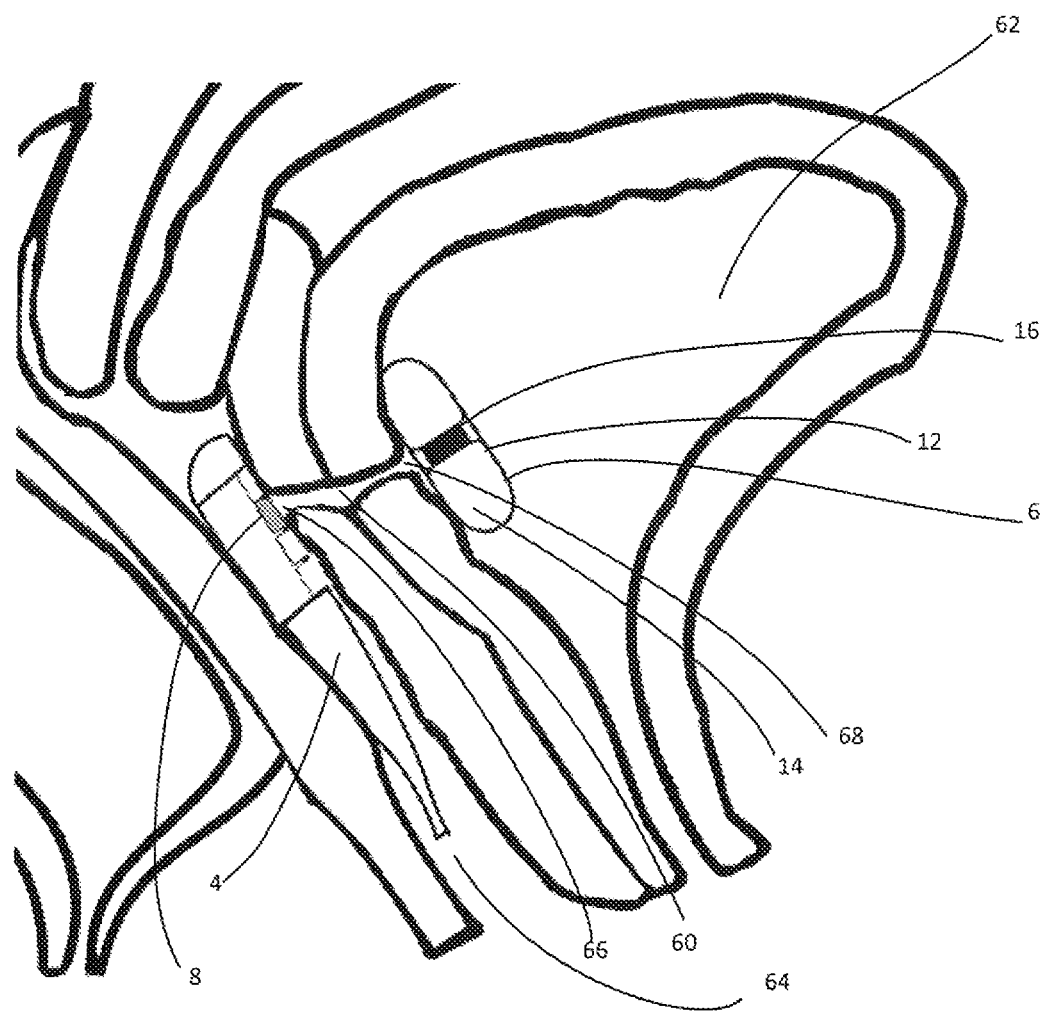
FIG. 7 shows use of the system of FIGS. 5a and 5b in the treatment of a fistula between the urinary bladder and the vagina of a female individual.

FIG. 7 shows use of the system 2 in the treatment of a vesicovaginal fistula 60 that has formed between the urinary bladder 62 and the vagina 64 of a female individual. For the treatment of the fistula with the invented system, prior to insertion of the vaginal and vesicular elements into the body, the mucosal layer covering the fistula tract may be removed using a fistula brush. The vesicular element 6 is shown after having been inserted into the urinary bladder 62 and expanded inside the bladder, as explained above. The vaginal element 4 has been inserted into the vagina 64 with its magnet 8 positioned at the level of the vaginal opening 66 of the fistula 60. Proper positioning of the vaginal element magnet 8 in the vagina is facilitated by selecting an appropriate retention site 3 (FIGS. 5*a* and 6) to position the magnet 8 adjacent to the fistula 60. The vesicular magnet 16 and the vaginal magnet 8 are positioned with opposite poles facing each other. Due to the mutual attraction between the magnet 8 located inside the vaginal element 4 and the magnet 16 in the vesicular element 6 the fistula tract is positioned between the two magnets. At the same time, the vesicular element 6 is positioned in the bladder 62 so as to obstruct the vesicular opening 68 of the fistula 60. With the vaginal element 4 and vesicular element 6 positioned as shown in FIG. 7, involuntary passage of urine from the bladder 62 to the vagina 64 through the fistula 60 tends to be reduced or eliminated.

The wall 12 of the vesicular element 6 may be made from any flexible biocompatible material, such as a medical grade silicone. The shape of the vesicular element 6 when expanded is selected to optimally conform to the topography of the bladder tissue surrounding the bladder opening 68 of the fistula 60. The inventors have found that flattened spherical shape tends to provide a larger foot-print and create a satisfactory seal of the bladder opening 68 of the fistula 60. The large axis of the balloon can be from 1 cm to 6 cm and is chosen according the diameter of the fistula.

Any biocompatible fluid may be used as an expansion fluid to expand the vesicular element. Preferably, the expansion fluid imparts to the expanded vesicular element 6 a specific gravity that is less than the specific gravity of urine, so that the expanded vesicular element 6 floats in urine. For example, the expansion fluid may be sterilized air, or a biocompatible oil such as mineral oil/liquid paraffin, vegetable oil or other oily substances. In one presently preferred embodiment, the wall 12 of the vesicular element 6 is made from a medical grade silicone and the expansion fluid is light mineral oil. The inventors have found that when the wall 12 of the vesicular element 6 is made from silicone, light mineral oil in the lumen 14 of the vesicular element 6 can slowly seep through the wall 12 of the vesicular element 6 and form a thin and smooth coating with zero stress on the exterior surface of the vesicular element 6 that tends to reduce or prevent the formation of biofilm and crystal adhesion on the vesicular element 6 which can cause infections.

As shown above, the inventors have observed acceleration of myotube formation in tissue cultures placed between two opposing magnetic fields. Hence, the magnetic fields surrounding the fistula 60 (FIG. 7) created by the two magnets 8 and 16 may induce accelerated bladder muscle tissue formation at the tissues surrounding the fistula 60, which may tend to close the fistula.

The magnet of the vaginal element and the magnet of the vesicular element will typically be separated by about 1 to 3 cm in use (FIG. 7). In vesicovaginal fistulae, a weaker magnetic field can provide an adequate force of attraction between the vaginal element and the vesicular element to maintain the two elements in the proper position and still be effective in tissue regeneration for the closure of the fistula tract.

The lower esophageal sphincter (LES) is a physiological sphincter at the distal part or the esophagus at the entrance to the stomach. A normally functioning LES prevents refluxing of stomach contents toward the esophagus. Weakening of this sphincter or a diaphragmatic hiatal herniation of the stomach causes reflux.

Figure 8A:
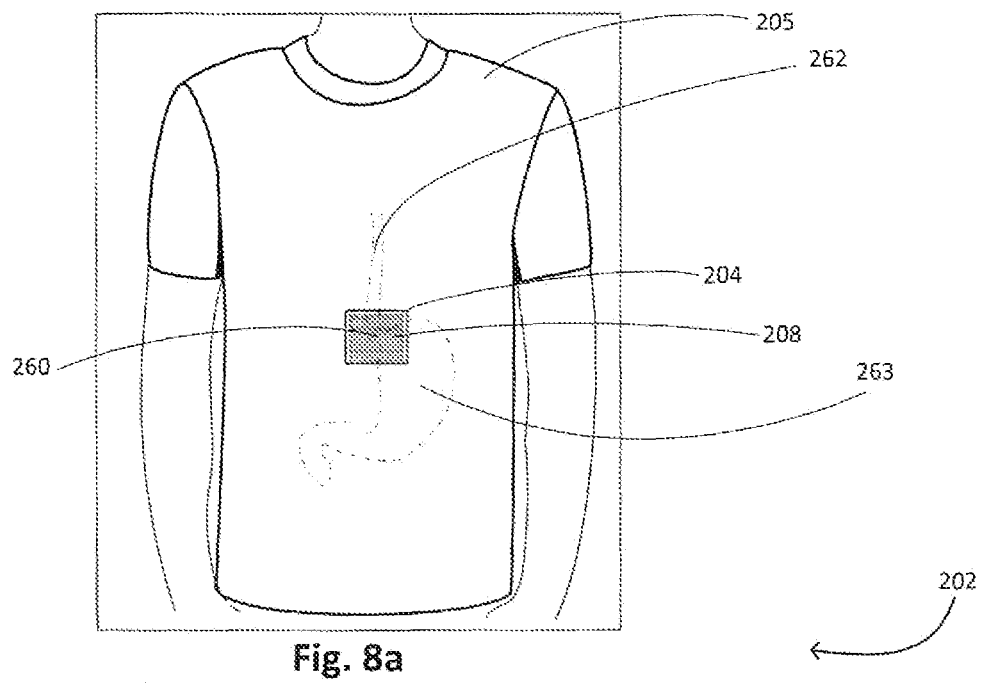
FIG. 8 shows use of a system for the treatment of a refluxing weak gastroesophageal sphincter in a front view (FIG. 8a), and a rear view (FIG. 8b)
Figure 8B:
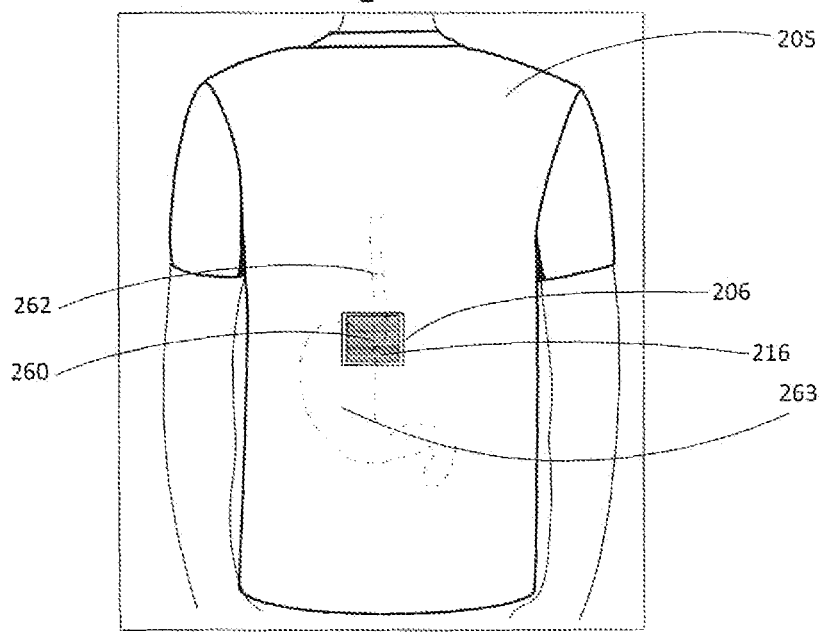

FIG. 8 shows use of a system 202 in the treatment of a weak gastroesophageal sphincter 260 between the esophagus 262 and the stomach 263 (shown in phantom lines in FIGS. 8*a* and 8*b*) of a male or female individual. The system 202 comprises a ventral magnetic element 204 and a dorsal magnetic element 206. The ventral and dorsal magnetic elements are incorporated into a garment, such as a belt, vest, sling or undershirt 205 that is worn by the individual. The ventral element 204 comprises a magnet 208, and the dorsal element 206 has a second magnet 216. The sling or garment 205, after having been donned by the individual, is shown in a front view in FIG. 8*a* and in a rear view in FIG. 8*b*. The ventral element 204 has been immobilized on the ventral body surface over the gastroesophageal sphincter 260 and the dorsal element 206 has been immobilized on the dorsal body surface over the gastroesophageal sphincter 260.

The magnetic field surrounding the gastroesophageal sphincter 260 by the two opposing magnets 208 and 216 may induce muscle tissue formation of the lower gastroesophageal sphincter and the muscle of the diaphragm, which may tend to strengthen the sphincter and reduce or eliminate gastroesophageal reflux disease (GERD).

The invention claimed is:

1. A system for inducing the formation of muscle tissue in a body organ, the system adapted for inducing muscle tissue formation of a urinary bladder sphincter, the system comprising:
   a first magnet producing a first static magnetic field;
   a second magnet producing a second static magnetic field;
   one or more devices configured to immobilize the first magnet on a first side of the body organ and to immobilize the second magnet on a second side of the body organ, wherein a pole of the first magnet faces an opposite pole of the second magnet;
   wherein a first element, which is an external element comprising the first magnet, is physically adapted for immobilization on an external body surface of the individual below the urinary bladder at a downstream part of the urethral sphincter;
   wherein a second element is a vesicular element, which comprises the second magnet, is physically adapted to be immobilized at the urinary bladder outlet inside the bladder; and
   wherein the vesicular element further comprises a balloon configured to be filled in the urinary bladder of the individual.

2. The system according to claim 1 wherein the external element is incorporated into a garment configured to be worn by the individual.

3. A system for inducing the formation of muscle tissue in a body organ, the system adapted for inducing muscle tissue formation of a urinary bladder sphincter, the system comprising:
   a first magnet producing a first static magnetic field;
   a second magnet producing a second static magnetic field;
   one or more devices configured to immobilize the first magnet on a first side of the body organ and to immobilize the second magnet on a second side of the body organ, wherein a pole of the first magnet faces an opposite pole of the second magnet;
   wherein a first element, which is an external element comprising the first magnet, is physically adapted for immobilization on an external body surface of the individual below the urinary bladder at a downstream part of the urethral sphincter;

wherein a second element is a vesicular element, which comprises the second magnet, is physically adapted to be immobilized at the urinary bladder outlet inside the bladder; and wherein:

the first element is a ventral element;

the second element is a dorsal element; and the ventral and dorsal elements are incorporated into a garment, vest, undershirt, belt or sling.

4. The system according to claim 1 adapted for treatment of a vesicovaginal fistula in a female individual.

5. The system according to claim 4 wherein:

a first element, which is a vaginal element comprising the first magnet, is physically adapted to be retained in the vagina adjacent to a vaginal side of the fistula; and a second element is a vesicular element, which comprises the second magnet, is physically adapted to be immobilized in the urinary bladder on the bladder side of the fistula.

6. The system according to claim 5 wherein:

the first magnet is enclosed in a biocompatible coating for promoting retention of the vaginal element in the vagina; and the vesicular element is a balloon configured to be filled with a fluid in the urinary bladder of the female individual.

7. The system according to claim 6 wherein the vaginal element has a handle.

8. The system according to claim 6 wherein the vaginal element has one or more retention sites, each retention site being configured for retaining the first magnet.

9. A system for inducing the formation of muscle tissue in a body organ, the system adapted for inducing muscle tissue formation of a urinary bladder sphincter, the system comprising:

a first magnet producing a first static magnetic field;

a second magnet producing a second static magnetic field; and one or more devices configured to immobilize the first magnet on a first side of the body organ and to immobilize the second magnet on a second side of the body organ, wherein a pole of the first magnet faces an opposite pole of the second magnet;

wherein a first element, which is an external element comprising the first magnet, is physically adapted for immobilization on an external body surface of the individual below the urinary bladder at a downstream part of the urethral sphincter;

wherein a second element is a vesicular element, which comprises the second magnet, is physically adapted to be immobilized at the urinary bladder outlet inside the bladder;

wherein the vesicular element further comprises a balloon configured to be filled in the urinary bladder of the individual, wherein the balloon has a shape when filled that is selected from the group consisting of spherical, spherical having one or two dimples and a disc shape.

10. The system according to claim 6 wherein the balloon has a shape when filled that is selected from the group consisting of spherical, spherical having one or two dimples, and a disc shape.

11. The system according to claim 1 wherein the balloon comprises a self-sealing valve for filing the balloon.

12. The system according to claim 6 wherein the balloon comprises a self-sealing valve for filling the balloon.

13. The system according to claim 1 wherein the sphincter is a urinary bladder sphincter, and further wherein:

a first element, which is an external element comprising the first magnet, is physically adapted for immobilization on an external body surface of the individual below the urinary bladder at a downstream part of the urethral sphincter; and a second element is a vesicular element, which comprises the second magnet, is physically adapted to be immobilized at the urinary bladder outlet inside the bladder.

14. The system according to claim 1 adapted for treatment of a vesicovaginal fistula in a female individual, wherein:

a first element, which is a vaginal element comprising the first magnet, is physically adapted to be retained in the vagina adjacent to a vaginal side of the fistula; and a second element is a vesicular element, which comprises the second magnet, is physically adapted to be immobilized in the urinary bladder on the bladder side of the fistula.

* * * * *